United States Patent [19]
Hesse

[11] Patent Number: 5,866,401
[45] Date of Patent: Feb. 2, 1999

[54] PORCINE REPRODUCTIVE AND RESPIRATORY SYNDROME VACCINE

[75] Inventor: Richard A. Hesse, Omaha, Nebr.

[73] Assignee: Schering Corporation, Kenilworth, N.J.

[21] Appl. No.: 805,087

[22] Filed: Feb. 24, 1997

Related U.S. Application Data

[60] Provisional application No. 60/012,642 Mar. 1, 1996.

[51] Int. Cl.[6] .............................. C12N 7/08; C12N 7/01; C12N 7/00; C12N 7/02
[52] U.S. Cl. ..................... 435/237; 435/235.1; 435/236; 435/239; 424/199.1; 424/204.1
[58] Field of Search ............................. 424/204.1, 199.1; 435/235.1, 236, 237, 238, 240.2

[56] References Cited

U.S. PATENT DOCUMENTS

| | | | |
|---|---|---|---|
| 5,476,778 | 12/1995 | Chladek et al. | 435/235.1 |
| 5,510,258 | 4/1996 | Sanderson | 435/237 |
| 5,587,164 | 12/1996 | Sanderson et al. | 424/218.1 |
| 5,677,429 | 10/1997 | Benfield | 530/388.3 |
| 5,683,865 | 11/1997 | Collins et al. | 435/5 |
| 5,690,940 | 11/1997 | Joo | 424/229.1 |
| 5,695,766 | 12/1997 | Paul et al. | 424/204.1 |
| 5,698,203 | 12/1997 | Visser et al. | 424/218.1 |

FOREIGN PATENT DOCUMENTS

| | | | |
|---|---|---|---|
| 0595436 | 5/1994 | European Pat. Off. | |
| 0676467 | 10/1995 | European Pat. Off. | |
| 2282811 | 4/1995 | United Kingdom | C12N 15/40 |
| 93/03760 | 3/1993 | WIPO | A61K 39/00 |
| WO93/07898 | 4/1993 | WIPO | |
| WO93/14196 | 7/1993 | WIPO | |
| WO94/18311 | 8/1994 | WIPO | |
| WO96/36356 | 11/1996 | WIPO | |
| WO97/00696 | 1/1997 | WIPO | |

OTHER PUBLICATIONS

Boehringer Ingelheim Product Sheet. ResPRRS/Repro., Aug. 15, 1996.

Yoon et al. "Failure to consider the antigenic diversity of porcine reproductive and respiratory syndrom (PRRSV) virus isolateds may lead to misdiagnosis". J. Vet. Diagn. Invest. vol. 7, pp. 386–387, Jul. 1995.

Nelson et al. "Differential of U.S. and European Isolates of Porcine Reproductive and Respiratory Syndrom Virus by Monoclonal Antibodies". Journal of Clinical Microbiology. vol. 31, No. 12, pp. 3184–3189, Dec. 1993.

Beilage, E.G., Deutsche Tierarzliche Wochenschrift, vol. 102, No. 12, 1995, pp. 457–469.

Nelson et al., Journal of Clinical Microbiology, vol. 31, No. 12, 1993, pp. 3184–3189.

Meng, X.–J. et al., Journal of General Virology, vol. 76, 1995, pp. 3181–3188.

*Primary Examiner*—Marian C. Knode
*Assistant Examiner*—Datquan Lee
*Attorney, Agent, or Firm*—Arthur Mann; John J. Maitner

[57] ABSTRACT

The invention discloses a vaccine and methods for the treatment of porcine reproductive and respiratory syndrome. The vaccine is derived from the viral agent NEB-1-P94, deposited at the American Type Culture Collection under accession number VR-2525.

Further, the invention discloses a vaccine virus with phenotypic characteristics which can be distinguished from wild type PRRS virus.

4 Claims, No Drawings

PORCINE REPRODUCTIVE AND RESPIRATORY SYNDROME VACCINE

This application claims the benefit of U.S. Provisional application No. 06/012,642, filed Mar. 1, 1996.

BACKGROUND OF THE INVENTION

The present invention relates to a vaccine for the treatment of porcine reproductive and respiratory syndrome (PRRS).

In 1987, the swine-producing industry in the United States experienced an unknown infectious disease which had a serious economic impact on the swine industry. The disease syndrome was reported in Europe including Germany, Belgium, the Netherlands, Spain and England.

The disease is characterized by reproductive failure, respiratory disease and various clinical signs including loss of appetite, fever, dyspnea, and mild neurologic signs. A major component of the syndrome is reproductive failure which manifests itself as premature births, late term abortions, pigs born weak, stillbirths, mummified fetuses, decreased farrowing rates, and delayed return of estrus. Clinical signs of respiratory disease are most pronounced in pigs under 3-weeks-of-age but are reported to occur in pigs at all stages of production. Affected piglets grow slowly, have roughened hair coats, respiratory distress ("thumping"), and increased mortality.

The disease syndrome has been referred to by many different terms including mystery swine disease (MSD), porcine epidemic abortion and respiratory syndrome (PEARS), swine infertility and respiratory syndrome (SIRS). The name now commonly used is porcine reproductive and respiratory syndrome (PRRS); this term will be employed throughout this patent application.

It is an object of the invention to provide a vaccine which protects a pig against clinical disease caused by PRRS. Another object is to provide a vaccine which, when administered to a breeding swine herd, will reduce the presence of PRRS in their population.

SUMMARY OF THE INVENTION

An object of the present invention is to provide a novel vaccine which protects a pig against clinical disease caused by porcine reproductive and respiratory syndrome (PRRS) virus.

A further object of the present invention is to provide a vaccine which protects a pig against the strain NEB-1 of PRRS virus.

It is a further object of the present invention to provide a method of protecting a pig against clinical disease caused by a porcine reproductive and respiratory disease virus.

It is a further object of this invention to provide a vaccine virus with phenotypic characteristics which can be distinguished from wild type PRRS virus.

DETAILED DESCRIPTION OF THE INVENTION

The invention provides a composition of matter comprising an attenuated Porcine Respiratory and Reproductive Syndrome (PRRS) Virus which has been modified by laboratory manipulation for use in vaccination. Further the composition has phenotypic properties which allow its use for diagnostic purposes to distinguish between swine that have been naturally-infected with PRRS virus versus animals that have only been exposed to the vaccine strain. The PRRS virus isolate NEB-1-P94 has been deposited with American Type Culture Collection 12301 Parklawn Drive, Rockville, Md. 20852, U.S.A. (Accession No. VR-2525) on Mar. 1, 1996.

A virulent isolate of PRRS virus was obtained from tissue samples from a dead pig presented to the University of Nebraska Diagnostic Laboratory. A tissue homogenate from the dead pig was inoculated onto primary swine alveolar macrophages and the presence of virus detected by cytopathic effects on inoculated but not control cultures. The isolated virus (designated NEB-1) was subsequently characterized as a PRRS virus based on physical properties (ether and chloroform sensitivity, buoyant density, and lack of hemagglutinating activity), reactivity with specific antibodies, and genetic analysis. Inoculation of the virus into nursing piglets resulted in a respiratory disease characterized by high fever, altered respiration and lung pathology consistent with viral interstitial pneumonia. Additionally, inoculation of the virus into pregnant sows resulted in reproductive disease characterized by mummification of fetuses, stillborn piglets, and piglets born weak that subsequently died. The respiratory and reproductive disease caused by this virus was typical of the syndrome reported for PRRS virus.

The NEB-1 virus was attenuated by serial passage in tissue culture. The virus was initially passed by inoculation of primary swine alveolar macrophage (SAM) cultures (for the first two passages) and then by serial passage on MA104 cells (available from Microbiological Associates, Inc., Rockville, Md.) for a total of 94 passages. During this process, virus clones were isolated by plaque purification and characterized for phenotypic properties. The vaccine clone, designated NEB-1-P94, was selected for impaired growth on swine alveolar macrophages, lack of reactivity with the PRRS-specific monoclonal antibody SDOW17 (ATCC HB10997), and lack of disease induction in piglets and pregnant sows. The NEB-1-P94 was expanded on MA104 cells and frozen as a master seed virus, also designated PRRS-MSV-94-1, for use in vaccine development studies.

Vaccine is prepared using MA104 cells as the substrate (however alternate cell lines that support the growth of PRRS virus such as MARC 145 [available from Dr. Wang, Agriculture Research Station, Clay Center NE] cells can also be used). MA104 cells are grown to confluency in suitable tissue culture vessels, e.g. 850 $cm^2$ roller bottles, using Eagle's minimum essential media (EMEM) containing 5 to 10% bovine serum, 30 mM HEPES (N-2-hydroxyethylpiperazine-N'-2-ethanesulfonic acid, 2 mM L-glutamine, and antibiotics (such as 30 $\mu$g/ml gentamicin). Alternate tissue culture media that can support the growth of MA104 cells such as Dulbecco's modified essential media [DMEM], Medium 199, or others can also be used. Confluent monolayers of MA104 cells are inoculated with NEB-1-P94 virus at a multiplicity of infection (MOI) in the range of 1:5 to 1:1000, and, preferably in the range of 1:10. Following incubation for three to five days at 37° C., culture supernatant fluids are harvested by decanting.

Virus fluids are titered by making serial dilutions in EMEM supplemented as above and inoculation of 0.2 ml per well into at least four replicate wells of confluent MA104 or MARC 145 cells in a 96-well tissue culture plate. Cultures are incubated for five days at 37° C., 3–5% $CO_2$ in a humidified chamber and observed for cytopathic effects. Titers (50% endpoints) are calculated according to the methods of Spearman and Karber (Methods in Virology, Volume IV, K. Maramorosch and H. Koprowski (Eds). Academic Press, New York, 1977). Cells may be fixed with 80% acetone and tested for lack of reactivity with SDOW17 and positive reactivity with V017 or EP147 (available from Dr. E. Nelson, South Dakota State University, Brookings, S. Dak.) (expected positive result) monoclonal antibodies to confirm phenotypic identity of the virus.

For the preparation of a killed vaccine, virus fluids are incubated with a chemical inactivation agent. Examples of inactivation agents include formaldehyde, glutaraldehyde, binary ethyleneimine, or beta-propiolactone. Virus fluids are then stored at 4° C. until formulated into vaccine. Vaccine is prepared by mixing virus fluids (containing $10^6$ to $10^9$ $TCID_{50}$ of virus; based on preinactivation titers) with a physiologically acceptable diluent (such as EMEM, Hank's Balanced Salt Solution, Phosphate Buffered Saline) and an immune-stimulating adjuvant (such as mineral oil, vegetable oil, aluminum hydroxide, saponin, non-ionic detergents, squalene, block co-polymers or other compounds known in the art, used alone or in combination). A vaccine dose is typically between 1 and 5 ml.

For a live vaccine formulation, virus fluids are stored frozen at −50° C. or colder until use. Virus fluids within the range of $10^{4.0}$ and $10^{7.0}$ $TCID_{50}$/dose and preferably containing $10^{6.0}$ $TCID_{50}$/dose are diluted with a physiologically suitable diluent (such as EMEM, Hank's Balanced Salt Solution, Phosphate Buffered Saline) and a physiologically suitable mixture of compounds designed to stabilize the virus. Compounds known in the art that can be used alone or in combination to stabilize viruses include sucrose, lactose, N-Z amine, glutathione, neopeptone, gelatin, dextran and tryptone. Vaccine is stored frozen (−50° C. or colder) or lyophilized with storage at 4° C. until use. The vaccine typically has a dose size range of 1 to 5 ml, and preferably 2 ml.

For prophylaxis against PRRS-induced disease, the vaccine is administered to the pig orally, intranasally or parenterally. Examples of parenteral routes of administration include intradermal, intramuscular, intravenous, intraperitoneal and subcutaneous routes of administration.

When administered as a solution, the present vaccine may be prepared in the form of an aqueous solution, a syrup, an elixir, or a tincture. Such formulations are known in the art, and are prepared by dissolution of the antigen and other appropriate additives in the appropriate solvent systems. Such solvents include water, saline, ethanol, ethylene glycol, glycerol, A1 fluid, etc. Suitable additives known in the art include certified dyes, flavors, sweeteners, and antimicrobial preservatives, such as thimerosal (sodium ethylmercurithiosalicylate). Such solutions may be stabilized, for example, by addition of partially hydrolyzed gelatin, sorbitol, or cell culture medium, and may be buffered by methods known in the art, using reagents known in the art, such as sodium hydrogen phosphate, sodium dihydrogen phosphate, potassium hydrogen phosphate and/or potassium dihydrogen phosphate.

Liquid formulations may also include suspensions and emulsions. The preparation of suspensions, for example using a colloid mill, and emulsions, for example using a homogenizer, is known in the art.

Parenteral dosage forms, designed for injection into body fluid systems, require proper isotonicity and pH buffering to the corresponding levels of porcine body fluids. Parenteral formulations must also be sterilized prior to use.

Isotonicity can be adjusted with sodium chloride and other salts as needed. Other solvents, such as ethanol or propylene glycol, can be used to increase solubility of ingredients of the composition and stability of the solution. Further additives which can be used in the present formulation include dextrose, conventional antioxidants and conventional chelating agents, such as ethylenediamine tetraacetic acid (EDTA).

A booster vaccination may be administered two to four weeks after the initial immunization. For the prevention of reproductive disease, the vaccination regimen is typically performed up to 6 weeks prior to and 1 week after breeding. For the prevention of respiratory disease in piglets, vaccination may be given as early as 3 weeks of age. The response to vaccination can be monitored by measuring antibody titer directed against PRRS virus using enzyme-linked immunosorbent assay (ELISA), serum neutralization assay, indirect immunofluorescence, or Western blot.

The vaccine strain has phenotypic properties that can be used for diagnosis in swine of wild type PRRS infection versus exposure to only the vaccine strain. Animals exposed to field strains of PRRS virus may be distinguished from animals exposed only to the NEB-1-P94 vaccine strain by measurement of the antibody response to the epitope recognized by monoclonal antibody (MAb) SDOW17. The presence of antibodies reactive with the SDOW17 epitope is indicative of wild type virus exposure, Measurement of antibodies to the SDOW17 epitope can be accomplished using a competitive ELISA. Plates (96-well) are coated with the NEB-1 PRRS virus (or other PRRS viruses expressing the SDOW17 epitope). Plates are then incubated with pig serum from test animals and enzyme-labelled (for example conjugated to horseradish peroxidase) SDOW17 monoclonal antibody. The ability of pig sera to recognize the SDOW17 epitope is measured by the inhibition of enzyme-linked SDOW17 MAb binding to the plate as detected by lack of enzyme substrate color conversion. Alternatively, a direct ELISA may be used. The amino acid sequence comprising the SDOW17 epitope can be prepared as a synthetic peptide or by recombinant DNA expression methods in a suitable vector system such as *E. coli*. Plates coated with the SDOW17 antigen are incubated with pig serum. Binding of swine antibodies to the SDOW17 antigen is detected by incubation with enzyme-conjugated anti-swine immunoglobulin antisera followed by incubation with enzyme substrate and detection of a color change.

The following examples describe in detail the invention. It will be apparent to those skilled in the art that modification of materials and methods may be practiced without departing from the purpose and intent of this disclosure.

EXAMPLE 1

Phenotypic Characterization of NEB-1-P94 for Growth on Alveolar Macrophages

The NEB-1-P94 vaccine strain virus at five passages from the master seed was characterized for growth on MA104, MARC 145, and swine alveolar macrophages. Swine alveolar macrophages (SAM) were obtained by bronchi-alveolar lavage with saline followed by centrifugation to pellet the cells. Macrophages were resuspended in EMEM with 10% fetal bovine serum and 50 μg/ml gentamicin and plated at approximately $7 \times 10^4$ cells per well of 96-well tissue culture plates. MA104 cells and MARC 145 cells were plated in 96-well tissue culture plates in media (EMEM containing 10% fetal bovine serum, 30 mM HEPES, 2 mM L-glutamine, and 50 μg/ml gentamicin). NEB-1-P94 or the parental NEB-1 virus were serially diluted in media and 0.2 ml of each dilution inoculated into replicate wells of 96-well plates containing SAM, MA104, or MARC 145 cells. Cultures were incubated for 5 days at 37° C., 3% to 5% $CO_2$, in a humidified chamber and monitored for cytopathic effects typical of PRRS virus. Titers (50% endpoints) were calculated according to the method of Spearman and Karber. The NEB-1-P94 showed reduced titers or unmeasurable titers on three separate SAM cultures compared to the titers obtained on MA104 and MARC 145 cells (Table 1). This is a phenotypic change compared to the parental strain which showed similar titers on all of the cultures tested. Therefore, impaired growth on swine alveolar macrophages was a selected phenotypic marker for the vaccine strain NEB-1-P94.

TABLE 1

Comparison of Growth of the NEB-1-P94 Virus on Various Cell Types

| Virus | Titer* on MA104 | Titer* on MARC 145 | Titer* on SAM 7 | Titer* on SAM 8 | Titer* on SAM 22 |
|---|---|---|---|---|---|
| NEB-1-P94 | 5.3 | 6.1 | ≦1.2 | 2.5 | <1.2 |
| NEB-1 | 5.2 | 6.5 | 5.2 | 6.5 | 6.5 |

*Titer = $\log_{10}$ TCID$_{50}$/ml (limit of detection in this assay = 1.2)

EXAMPLE 2

Phenotypic Characterization of NEB-1-P94 for Lack of Virulence in Swine

Four gnotobiotic piglets (seven to 10 days of age) from PRRS seronegative sows were inoculated intranasally (3 ml/nare) with NEB-1-P94 master seed virus ($10^{5.3}$ TCID$_{50}$/ml). Piglets were observed for clinical signs of respiratory disease and the vaccine strain virus was re-isolated from serum at five days post-inoculation. Serum from the first group of pigs was used to intranasally inoculate a second group of gnotobiotic pigs which were monitored in the same way. This process was repeated for a total of five serial backpassages in piglets in order to determine whether the vaccine strain could revert to a virulent state. Vaccine virus was recovered from each successive animal passage, however, respiratory disease was not observed in the gnotobiotic pigs. In addition, virus isolated from the fifth backpassage pigs was intranasally inoculated into one-week-old and three-week-old conventional piglets (approximately $10^{5.3}$ TCID$_{50}$/ml was administered per piglet). Animals were monitored for 42 days after virus inoculation and no clinical disease signs (i.e. prolonged high fever, respiratory signs, lung lesions) consistent with virulent PRRS infection were found. Therefore, the NEB-1-P94 virus was concluded to be avirulent for induction of respiratory disease in piglets.

Next the NEB-1-P94 virus was examined for its ability to cause reproductive disease. PRRS seronegative sows at 85 days of gestation were inoculated intranasally (3 ml/nare) with the master seed vaccine strain ($10^{4.5}$ TCID$_{50}$/ml). All sows farrowed at their expected time and 96% of the piglets were born live and healthy. By comparison, uninoculated control sows gave birth to litters where 87% of the piglets were live and healthy. Therefore, the vaccine strain NEB-1-P94 failed to induced reproduction disease typical of a virulent PRRS virus (See Example 4). These data confirmed the avirulent phenotype of the vaccine strain, NEB-1-P94.

EXAMPLE 3

Phenotypic Characterization of NEB-1-P94 for Reactivity with PRRS Virus-Specific Monoclonal Antibodies MA104 cells infected with parental strain NEB-1 or the vaccine strain NEB-1-P94 virus were examined for reactivity with monoclonal antibodies specific for the PRRS virus by indirect immunofluorescence. Briefly, 96-well plates of confluent MA104 cells were fixed with 80% acetone for 10 minutes at 2 days after infection with each virus. Monolayers were then incubated with SDOW17, V017, or EP147 monoclonal antibodies. Following washing, monoclonal antibody reactivity with each virus was detected by incubation with fluorescein isothiocyanate conjugated anti-mouse IgG followed by washing and examination for fluorescence by microscopy. Positive fluorescence was noted with all three monoclonal antibodies for the NEB-1 parental strain (Table 2). However, the vaccine strain, NEB-1-P94, had lost reactivity with the SDOW17 monoclonal antibody but tested positive with the other two monoclonal antibodies. These data indicate that the NEB-1-P94 strain had lost expression of epitope recognized by the SDOW17 antibody. The loss of reactivity with this monoclonal antibody most likely represents genetic mutation in the RNA sequence of NEB-1-P94 which resulted in an altered amino acid sequence in the nucleocapsid protein region recognized by SDOW17.

TABLE 2

Reactivity of Parental and Vaccine Strain PRRS with Specific Monoclonal Antibodies.

| | Reactivity with SDOW17 | Reactivity with VO17 | Reactivity with EP147 |
|---|---|---|---|
| NEB-1-P94 | − | + | + |
| NEB-1 | + | + | + |

EXAMPLE 4

Prevention of Reproductive Disease by Vaccination of Sows with NEB-1-P94

Vaccine was prepared by inoculation of confluent roller bottles of MA104 cells with NEB-1-P94 (4 passages from the master seed) at a multiplicity of infection of approximately 1:10 in EMEM containing 10% fetal bovine serum, 2 mM L-glutamine, and 30 μg/ml gentamicin. Cultures were incubated for three days at 37° C. and then supernatant fluids were harvested by decanting. Virus fluids were diluted 50% (v/v) with stabilizer (75 g/L tryptone, 30 g/L dextran, 2 g/L gelatin, 100 g/L lactose, 2 g/L sodium glutamate, 1.05 g/L KH$_2$PO$_4$, 2.5 g/L K$_2$HPO$_4$, 10 g/L albumin fraction V), frozen, and lyophilized. Vaccine was rehydrated with sterile deionized water and 2 ml ($10^{5.1}$ TCID$_{50}$/ml) administered intramuscularly to gilts four to six weeks prior to breeding.

At 85 days of gestation, vaccinated and unvaccinated control gilts were challenged by intranasal administration of NEB-1 virus (approximately $10^{6.3}$ TCID$_{50}$). Animals were monitored through seven weeks after farrowing for signs of fetal or neonatal death attributed to PRRS virus. PRRS viremia developed in 11/12 (92%) of control sows and 100% of their live-born piglets. PRRS infection during pregnancy resulted in 16% death loss at parturition (large mummies and stillborn pigs) in the control group (Table 3) compared to only 6% death loss in vaccinated sows. In addition, vaccination resulted in a 50% reduction in the incidence of weak and shaky piglets and 94% reduction in piglets with low birth weights (weighing less than 2 pounds at birth) when compared to controls. Vaccination prevented congenital PRRS as evidenced by the absence of PRRS virus in blood or tissues of any piglets from immunized sows and a 55% prevention of death loss through 7 weeks of age (Table 3) when compared to controls. The statistically significant prevention of death loss and virus infection in vaccinated sows and their offspring clearly demonstrated the efficacy of this vaccine in preventing the reproductive form of PRRS virus-induced disease.

animals. Vaccination resulted in a statistically significant reduction in fever, respiratory signs, and clinical illness in vaccinated animals compared to controls (Table 4). This study clearly demonstrated the efficacy of the vaccine in the prevention of respiratory disease caused by PRRS virus in young pigs.

TABLE 3

Summary of Reproductive Disease Noted After PRRS Virus Challenge of Vaccinated versus Control Sows

| Group | Number of Sows (Ave # Pigs/Litter) | % Large Mummies and Stillborn | % Born Live but Died | % Weak and Shaky | % Piglets Weighing <2 lbs. | 7 Week Mortality |
|---|---|---|---|---|---|---|
| Vaccinated | 21 (10.8) | 6% | 2% | 3% | 1% | 17% |
| Controls | 12 (10.1) | 16% | 3% | 6% | 17% | 38% |

EXAMPLE 5

Prevention of Respiratory Disease by Vaccination of Sows with NEB-1-P94

Vaccine was prepared by inoculation of confluent roller bottles of MA104 cells with NEB-1-P94 (at 4 passages from the master seed) at a multiplicity of infection of approximately 1:10 in EMEM containing 10% fetal bovine serum, 2 mM L-glutamine, and 30 μg/ml gentamicin. Cultures were incubated for five days at 37° C. and then supernatant fluids were harvested by decanting. Virus fluids were diluted 50% (v/v) with stabilizer (75 g/L tryptone, 30 g/L dextran, 2 g/L gelatin, 100 g/L lactose, 2 g/L sodium glutamate, 1.05 g/L KH2PO4, 2.5 g/L K$_2$HPO$_4$, 10 g/L albumin fraction V), frozen, and lyophilized. Vaccine was rehydrated with sterile deionized water and 1 ml ($10^{4.9}$ TCID$_{50}$/ml) administered intramuscularly to PRRS seronegative piglets at three weeks of age.

Four weeks following vaccination, piglets were challenged with virulent NEB-1 PRRS virus by intranasal route as described for gilts (Example 4). Piglets were monitored for respiratory disease signs for 14 days after challenge. All unvaccinated control piglets developed clinical signs of respiratory disease compared with 3/40 (8%) of vaccinated

TABLE 4

Summary of Clinical Disease in Vaccinated and Control Animals Following PRRS Virus Challenge Percentage of Animals with Clinical Signs on Indicated Days

| | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Respiratory Signs | | | | | | | | | | | | | | | |
| Controls | 0 | 0 | 0 | 57 | 53 | 37 | 60 | 40 | 37 | 40 | 47 | 40 | 23 | 30 | 33 |
| Vaccinates | 0 | 0 | 0 | 8 | 8 | 0 | 2 | 8 | 0 | 2 | 5 | 5 | 5 | 2 | 0 |
| Fever >104.5° F. | | | | | | | | | | | | | | | |
| Controls | 3 | 17 | 43 | 73 | 83 | 73 | 66 | 50 | 37 | 57 | 47 | 37 | 20 | 17 | NA |
| Vaccinates | 0 | 14 | 20 | 20 | 14 | 10 | 10 | 20 | 2 | 14 | 10 | 10 | 4 | 4 | NA |
| Clinical Illness | | | | | | | | | | | | | | | |
| Controls | 0 | 0 | 0 | 23 | 60 | 50 | 60 | 47 | 33 | 50 | 50 | 40 | 33 | 27 | 33 |
| Vaccinates | 0 | 0 | 0 | 2 | 0 | 0 | 0 | 2 | 0 | 2 | 2 | 2 | 0 | 0 | 0 |

NA = Data not available
Controls n = 30
Vaccinates n = 40

I claim:

1. A vaccine suitable for immunizing swine against porcine reproductive and respiratory syndrome comprising a PRRS virus having all the identifying characteristics of the isolate NEB- 1 -P94, deposited at the American Type Culture Collection under the accession number VR-2525.

2. The vaccine of claim 1 containing an amount of $10^{4.0}$ to $10^{9.0}$ TCID$^{50}$ of the PRRS virus per ml.

3. A method of protecting a pig from clinical signs of disease caused by the porcine reproductive and respiratory syndrome virus comprising administering an effective amount of the vaccine of claim 1 to a pig.

4. The method of claim 3 wherein said vaccine is administered intramuscularly, intradermally, intravenously, or subcutaneously.

* * * * *